US006329428B1

(12) United States Patent
Yamauchi et al.

(10) Patent No.: US 6,329,428 B1
(45) Date of Patent: Dec. 11, 2001

(54) THERAPEUTIC DRUG FOR THE TREATMENT OF MICTURITION DISORDERS

(75) Inventors: Tamio Yamauchi, Suita; Tomohiro Ueda, Kyoto, both of (JP)

(73) Assignee: Taiho Pharmaceutical Co., Ltd., Tokyo (JP)

(*) Notice: Subject to any disclaimer, the term of this patent is extended or adjusted under 35 U.S.C. 154(b) by 0 days.

(21) Appl. No.: 09/582,791

(22) PCT Filed: Nov. 5, 1999

(86) PCT No.: PCT/JP99/06170

§ 371 Date: Jul. 5, 2000

§ 102(e) Date: Jul. 5, 2000

(87) PCT Pub. No.: WO00/27383

PCT Pub. Date: May 18, 2000

(30) Foreign Application Priority Data

Nov. 5, 1998 (JP) .................................................. 10-314369
Feb. 18, 1999 (JP) .................................................. 11-039779

(51) Int. Cl.[7] ........................... A61K 31/24; A61K 31/16
(52) U.S. Cl. ........................... 514/538; 514/599; 514/788; 514/741; 514/869; 514/968; 514/826
(58) Field of Search ..................................... 514/538, 599, 514/788, 741, 869, 968, 826

(56) References Cited

U.S. PATENT DOCUMENTS 5,475,033   12/1995   Ohmori et al. ....................... 514/599

FOREIGN PATENT DOCUMENTS

3408708   * 9/1984   (DE) .
WO 9633741   * 10/1996   (WO) .

OTHER PUBLICATIONS

Shindo et al. "Pharmacokinetic studies of suplatast tosylate (IPD–1151T). (III). Species differences of suplatast tosylate (IPD–1151T) and its metabolic pathways." Yakubutsu Dotai (1992), 7(4), 441–59.*

Ueda et al. "Improvement of interstitial cystitis symptoms and problems that developed during treatment with oral IPD–1151T." Journal of Urology, Dec.,2000, vol., 164, No. 6, pp. 1917–1920.*

Kuwata, Keizo et al, "Pharmacokinetic Studies of Suplatast tosilate (IPD–1151T) (I): Absorption, Distribution and Excretion after Administration of 14C–Suplatast tosilate (IPD–1151T) to Rats." Yakubutsu Dotai, 1992, vol. 7, No. 4, pp. 399–421.

International Search Report No date.

* cited by examiner

Primary Examiner—Ralph Gitomer
Assistant Examiner—Devesh Khare
(74) Attorney, Agent, or Firm—Sughrue, Mion, Zinn, Macpeak & Seas, PLLC

(57) ABSTRACT

The present invention is drawn to a therapeutic drug for micturition disorders and diseases of the lower urinary tract system, containing an organic acid salt of [2-[4-(3-ethoxy-2-hydroxypropoxy)phenylcarbamoyl]ethyl]-dimethylsulfonium. The invention enables treatment of diseases of the lower urinary tract system which cause urinary disorders, such as interstitial cystitis and prostatitis, which arise from unelucidated causes and thus are regarded intractable diseases.

34 Claims, No Drawings

THERAPEUTIC DRUG FOR THE TREATMENT OF MICTURITION DISORDERS

TECHNICAL FIELD

The present invention relates to a therapeutic drug for treating diseases of the lower urinary tract system, including those of the bladder and prostate, which can cause micturition disorders. The invention also relates to a therapeutic drug for micturition disorders accompanying these diseases.

BACKGROUND ART

Micturition disorder is a term which collectively refers to micturition-related pathological conditions, encompassing dysuria, pollakiuria, miction pain, and urinary incontinence.

Dysuria generally refers to a state where smooth urination is disturbed. Typical symptoms include: delay between the desire to void and the initiation of micturition; thin stream of urine, time for voiding prolonged; post-micturition dribble; conscious exertion of abdominal pressure needed to initiate voiding; and sense of residual urine remaining in the bladder immediately after urination. A special form of dysuria is urinary retention, which refers to a state in which voluntary micturition is disturbed and is characterized by retention of urine. Causes of urinary retention are broadly divided into (1) those attributed to neurological factors, including inco-ordination of the bladder smooth muscle and detrusor-sphincter dyssynergia, and (2) those attributed to organic factors, such as prostate-associated diseases, bladder neck sclerosis, and urethral stricture. Until today, however, the causes have not yet clearly elucidated and current theory holds that neurological changes and organic changes are closely related to each other. Thus, in order to formulate a remedy, studies should be directed not only at localized anatomy, but at the entire urinary system, including the bladder, the prostate, and the external sphincter (see *Medicine Journal*, vol. 33, S-1, 193–197 (1997).

Pollakiuria refers to a pathological condition in which frequency of urination rises to an abnormally high level. Frequency varies greatly from day to day among healthy individuals, and therefore, it is difficult to demarcate clearly. However, as a rough yardstick, frequency of more than ten times during the day and more than 2 times at during sleeping hours is regarded to be pollakiuria. Pollakiuria is sometimes accompanied by miction pain.

Miction pain is a pain felt along the urethra during micturition. Patients may experience this pain only at the initial or the final stage of voiding.

Urinary incontinence refers to a pathological condition where there is an involuntary letting of urine. There are several types of urinary incontinence: overflow incontinence where although the bladder is filled with urine normal micturition is inhibited and urine eventually overflows when a condition of urinary retention is reached; urge incontinence in which patients cannot suppress voiding once they have the desire to micturate; stress incontinence where incontinence occurs only when abdominal pressure is elevated; and true incontinence in which the bladder can no longer hold urine due to, for example, a dysfunction of the urethral sphincter. Urinary incontinence is often accompanied by pollakiuria.

Causes of micturition disorders include (1) disturbance of the nerves which control the bladder/urethral sphincter, which is attributed to, for example, spinal injuries, cerebrospinal tumors, cerebrospinal vascular disorders, myelitis, multiple sclerosis, Parkinson's disease, spinal meningoceles, radical surgery for uterine cancer, and radical surgery for colon cancer; (2) stimulation of the bladder membrane due to lesions in the bladder wall or inflammation or fibrosis of the muscle layers of the bladder, caused by cystitis, prostatitis, calculus at the lower end of the ureter, bladder cancer, etc. (3) injuries of the urethral sphincter; (4) obstructive lesions in the urethra attributed to prostatic hypertrophy. prostatic cancer, bladder neck sclerosis, or urethral stricture. Therapies for micturition disorders focus firstly on the treatment of underlying disorders/diseases. However, when such treatment is impossible, symptomatic treatment is usually attempted.

Among the above-mentioned causal disorders/diseases, diseases of the lower urinary tract system, such as lesions in the bladder wall or urethral obstructive lesions, such as cystitis, prostatitis, prostatic hypertrophy, bladder neck sclerosis, obstructive lesions, are intractable, and therefore there is a strong need for the development of effective pharmaceuticals.

Cystitis refers to infectious or non-infectious inflammation which primarily arises in the bladder membrane and submucosal tissue. In some cases, cystitis invades muscle layers. Generally, cystitis is divided into acute and chronic forms on the basis of clinical progress. Depending on the presence or absence of obstructive diseases in the lower urinary tract, cystitis is further classified into simple cystitis and complex cystitis. Generally, simple cystitis proceeds acutely and responds well to antimicrobial drugs. In contrast, complex cystitis proceeds chronically and often does not respond well to antimicrobial drugs, and is thus sometimes referred to as intractable cystitis. Intractable cystitis includes interstitial cystitis, hemorrhagic cystitis, bacterial intractable cystitis, and eosinocytic cytitis (see *Medicine Journal*, vol. 31, No. 3, 81–84 (1995)).

Interstitial cystitis is a disease of the bladder in which the present complaints (PC) include pain in the lower abdomen due to repletion of the bladder (bladder pain), pollakiuria, urinary urgency, or dysuria. These can be accompanied by complaints of a mental nature, including sensations of incomplete urination, malaise, depression, and anxiety, but are not accompanied by infection or peculiar pathological findings. In 1987, the National Institutes of Health (USA) provided guidelines—although thought to be incomplete—or diagnosing interstitial cystitis. According to the guidelines, causes of this disease, which have not been completely elucidated, include disturbance of the lymphatic system; chronic infection; disturbance of the nervous system; mental disorder; autoimmune disease; angiitis; toxic factors in the urine; compromised bladder defensemechanisms; and mast cells (*Clinical Urology*, Vol. 52, No. 9, 635–640, August, 1998). In the United States, about 500,000 patients currently suffer from interstitial cystitis and the American Urological Association includes in each of its conferences special sessions presenting the results of research into interstitial cystitis. The prevalence of interstitial cystitis is higher in women. Such female patients have difficulty in working and not infrequently become targets for firing and are subjected to sexual harassment. In Japan also, there may be many victims of interstitial cystitis. However, significant numbers of undiagnosed victims may be hidden among patients who complain of pollakiuria, in view that universal standards for diagnosis have not yet been established.

Current therapy for interstitial cystitis includes hydrodistention therapy; and drug therapy by use of drugs such as antidepressants, anti-histaminic agents, steroids, dimethyl sulfoxide (DMSO), and heparin. In hydrodistention therapy, the bladder is expanded through hydraulic pressure, and abatement is observed in approximately 50–60% of cases. However, after completion of the therapy, the condition may become aggravated in 2–3 weeks or may recur in 4–12 months. In such cases, the therapy must be repeated. Antidepressants elevate the patient's pain threshold and induce sleep. However, such drugs do not treat the underlying pollakiuria. Anti-histaminic agents have been used because it is believed that the development of interstitial cystitis is related to mast cells. However, it is accepted that these agents used alone rarely control the condition and must be used in combination with other therapies. Steroids, which are used for a comparatively large number of patients in Japan, are not drugs of first choice in Europe and the United States. This is because the optimum dose and administration duration of steroids have not been fully determined and their effects are unpredictable. DMSO is said to be effective for suppressing inflammation. It is reported that injection of DMSO into the bladder is effective in about 30–40% of cases and remission of the condition lasting for 5–6 years is observed (*J. Urol.*, 98, 671 (1986)). However, there are some cases of resistance to this therapy, and in such cases a subsequent treatment must be considered. In addition, results of animal tests indicate that DMSO may be in implicated in cataract formation although no such results have been reported in humans. Therefore, DMSO must be used with caution. Heparin is reported to be effective in about 50t of cases when used as intrabladder injection therapy (*Br. J. Urol.*, 73, 504–507 (1994)). However, this method is not readily acceptable as patients must be taught to self-catheterize to provide a route for injecting heparin into the bladder.

Hemorrhagic cystitis, another type of cystitis, is characterized primarily by the presence of heavy haematuria. It can be caused in a number of different ways. Main causes are 1) viruses such as adenovirus and influenz a virus, 2) microorganisms including bacteria such as *Escherichia coli*, Proteus, and *Pseudomonas aeruginosa*, 3) physical and chemical stimulation by radiation exposure or by the administration of drugs (cyclophosphamide, hexamine mandelate, methicillin, etc.). Previously, hemorrhagic cystitis was sometimes considered an allergic response. However, proving that a certain case of hemorrhagic cystitis is indeed an allergic response is not necessarily easy, and moreover, the frequency of cases that can be a ttributed to an allergic response remains unclear.

A typical example of bacterial intractable cystitis is bladder tuberculosis. Bladder tuberculosis exhibits clear symptoms of cystitis and pyuria, and conventional antibacterial agents are not effective remedies.

Eosinophilic cystitis exhibits symptoms similar to those of acute bacterial cystitis and pyuria, with urine culture testing negative. Antibacterial agents have no effect on eosinophilic cystitis. This pathological condition is caused by an allergic reaction against drugs having antiallergic properties. Typical examples of such drugs include Tranilast, but other antiallergic drugs may also induce cystitis. Pathologically, eosinophilic cystitis is characterized by dominant chronic inflammatory findings with no characteristic trait. Eosinophilic cystitis may be easily alleviated by withdrawing the drugs which induced the condition. However, when the condition is difficult to alleviate, administration of steroids, and ultimately cystectomy, must be performed.

Prostatitis is roughly categorized into acute prostatitis and chronic prostatitis.

The majority of acute prostatitis cases are caused by bacterial infection, with urinary tract infection via the urethra being the most common. Hematogenous infection or infection from surrounding organs are minor causes. Typical examples of inflammation-inducing bacteria include Gram-negative bacteria (particularly *Escherichia Coli*) and Gram-positive bacteria (staphylococcus). Histologically, edema, expansion, inflammatory cells infiltration, necrosis of intestinal epithelium, and formation of small abscesses are observed in a part or all of the prostate. In some cases, small abscesses may be fused to form large abscesses, invading and infiltrating surrounding organs. The symptoms of acute prostatitis include systemic symptoms such as chills, trepidation, and high fever, which induce an increase in peripheral leukocytes. Examples of localized symptoms of the condition include miction pain, pollakiuria, dysuria, and pain or unpleasant sensations in the perineal region. Concomitant swelling of the prostate may induce urinary retention.

Chronic prostatitis is classified into two types, which are, firstly, a condition where acute prostatitis becomes chronic and, secondly, where it proceeds as chronic prostatitis from its onset. Histologically, inflammatory infiltrate and hyperplasia of the connective tissue are observed, as well as constriction and obstruction of the lumen. When the condition lasts for a prolonged period of time, degeneration of the epithelium along with considerable fibrosis is observed. Few systemic symptoms are apparent, but the condition induces various local symptoms such as dysuria, pollakiuria, miction pain, unpleasant sensations after urination, pain, compressive sensations or generalized unpleasant sensations in the genitalia.

Prostatic hypertrophy refers to a pathological condition in which hypofunction of the prostate due to aging induces formation of fibromuscular or glandular nodules on glands surrounding the urethra. These nodules gradually enlarge, resulting in an overall enlargement of the prostate. Prostatic hypertrophy itself is a benign disease, but when the disease proceeds and the prostate expands, the disease causes obstruction of the urinary tract, which results in micturition disorders and renal dysfunction. Hitherto, many theories explaining the causes of prostatic hypertrophy have been proposed. Since the prostate is a sex-hormone-dependent organ, many studies have been carried out from this viewpoint. However, the details of the disease have not yet been elucidated.

The bladder neck is the portion ranging from the internal urethral opening to the starting point of the posterior urethra. Bladder neck sclerosis is a pathological condition in which the walls of this section become thick and hardened, thereby losing elasticity and constricting the lumen, resulting in micturition disorders. Pathological profiles include hypertrophy of smooth muscle bundles and growth of collagen fiber around the bladder neck, and in many cases, due to complications caused by inflammation, submucosal edemas and infiltration of inflammatory cells are observed. A variety of theories explaining the causes have been proposed, including aging; progress of sclerosis accelerated by inflammation of the prostate, posterior urethra, bladder neck, etc.; and the possible relation to prostate atrophy. Cases of secondary bladder neck sclerosis include those manifesting complications associated with neurogenic bladder, conditions which follow chronic inflammatory changes (in particular tuberculosis), and those caused by the invasion of malignant tumors such as prostate cancer. Currently, radical therapy is considered difficult.

DISCLOSURE OF THE IVENTION

In view of the foregoing, the present inventors have monitored the therapeutic effects of a variety of drugs on various types of micturition disorders. Quite surprisingly, they have found that organic acid salts of [2-[4-(3-ethoxy-2-hydroxypropoxy)phenylcarbamoyl]ethyl] dimethylsulfonium, a compound known as a therapeutic drug for the treatment bronchial asthma, atopic dermatitis, and allergic rhinitis, exhibit remarkable therapeutic effects on micturition disorders, including excellent effect of increasing the volume of urine per instance of voiding, amelioration of pollakiuria, and the elimination of miction pain or bladder pain. Moreover, the present inventors have found that the above compounds also exhibit therapeutic effects on diseases of the lower urinary tract system which cause the above-mentioned pathological conditions. The present invention has been accomplished on the basis of the above findings.

Accordingly, the present invention provides a therapeutic drug to treat diseases of the lower urinary tract system which cause micturition disorders, comprising as an active ingredient, an organic acid salt of [2-[4-(3-ethoxy-2-hydroxypropoxy)phenylcarbamoyl]ethyl] dimethylsulfonium (hereinafter referred to as spulatast).

The present invention also provides a therapeutic drug for the treatment of micturition disorders, comprising an organic acid salt of spulatast as an active ingredient.

The present invention also provides use of an organic acid salt of spulatast in the manufacture of a therapeutic drug for the treatment of diseases of the lower urinary tract, which diseases cause micturition disorders.

The present invention also provides use of an organic acid salt of spulatast in the manufacture of a therapeutic drug for the treatment of micturition disorders.

The present invention also provides a method for the treatment of diseases of the lower urinary tract, which diseases cause micturition disorders, characterized by the administering, to a patient in need thereof, of an organic acid salt of spulatast.

The present invention also provides a method for the treatment of micturition disorders, characterized by the administering, to a patient in need thereof, of an organic acid salt of spulatast.

BEST MODES FOR CARRYING OUT THE INVENTION

As mentioned above, spulatast, the active ingredient of the therapeutic drug of the present invention, exhibits an anti-allergic action (Japanese patent publication (kokoku) No. 3–70698), and is commercially available as a therapeutic drug for bronchial asthma, atopic dermatitis, and allergic rhinitis. However, no published report indicates that spulatast has been used—or suggests that spulatast can be used—in the treatment of micturition disorders.

Spulatast is used in the form of an organic acid salt. Examples of organic acids for forming the salt include organic sulfonic acids such as methanesulfonic acid, p-toluenesulfonic acid, camphorsulfonic acid, and 1,5-naphthalenedisulfonic acid; and carboxylic acids such as lactic acid, maleic acid, and malonic acid. Of these, organic sulfonic acids are preferred, with p-toluenesulfonic acid (tosyl acid) being particularly preferred.

Organic acid salts of suplatast effectively act on a variety of diseases of the lower urinary tract system, which diseases cause micturition disorders, and also on micturition disorders attributed to the diseases.

As used herein, the diseases of the lower urinary tract system on which the organic acid salts of suplatast act effectively refer to the diseases of the bladder, prostate, or the urethra. Diseases of the bladder include cystitis, bladder neck sclerosis, neurogenic bladder, and atrophic bladder. Diseases of the prostate include prostatitis and prostatic hypertrophy. Diseases of the urethra include urethritis and urethrostenosis. The diseases to which the present invention is applied are preferably those manifesting edemas, infiltration of inflammatory cells, or proliferation of spindle cells in the lower urinary tract, such as cystitis, bladder neck sclerosis, prostatitis, and prostatic hypertrophy, more preferably, those manifesting edemas, infiltration of inflammatory cells, or proliferation of spindle cells in the bladder or the prostate, and even more preferably, cystitis, prostatitis, and prostatic hypertrophy. Specifically, examples of cystitis include acute or chronic cystitis, interstitial cystitis, hemorrhagic cystitis, radiation cystitis, or bladder tuberculosis. Examples of prostatitis include acute and chronic prostatitis.

Organic acid salts of suplatast exhibit remarkable action in the treatment or prevention of a variety of symptoms of micturition disorders, including pollakiuria, urinary incontinence, miction pain, or bladder pain. Organic acid salts of suplatast significantly ameliorates, inter alia, predominant symptoms of micturition disorders—such as pollakiuria, miction pain, or bladder pain—caused by the aforementioned bladder- or prostate-associated diseases, bladder cancer, or prostatic cancer. More preferably, causal diseases are urethral obstructive lesions or bladder wall lesions such as acute or chronic cystitis, interstitial cystitis, hemorrhagic cystitis, radiation cystitis, bladder tuberculosis, bladder neck sclerosis, bladder cancer, acute or chronic prostatitis, prostatic hypertrophy, or prostatic cancer. Particularly preferably, causal diseases are acute or chronic cystitis, interstitial cystitis, hemorrhagic cystitis, radiation cystitis, bladder tuberculosis, bladder cancer, or acute or chronic prostatitis. Particularly notable effects on micturition disorders include an increased volume of urine per voiding, which ameliorates pollakiuria, and therapeutic or ameliorating effect of bladder pain.

In the present invention, therapeutic effects can be further improved when the organic acid salts of suplatast are used in combination with steroids. Moreover, in the treatment of chronic cystitis, interstitial cystitis, and chronic prostatitis, such a combination use can reduce the dosage of steroids, which is advantageous from the viewpoint of controlling side effects. Examples of steroids include those containing, as an active ingredient, prednisolone, methylprednisolone, methylprednisolone acetate, prednisolone valerate acetate, hydrocortisone, hydrocortisone acetate, hydrocortisone butyrate, hydrocortisone butyrate propionate, flumethasone pivalate, triamcinolone, triamcinolone acetonide, dexamethasone, dexamethasone acetate, dexamethasone valerate, dexamethasone propionate, fluocinolone, fluocinolone acetonide, betamethasone, betamethasone valerate, betamethasone dipropionate, beclomethasone propionate, clobetasone butyrate, fludroxycortide, fluocinonide, halcinonido, amcinonide, difluprednate, diflucortolone valerate, diflorasone acetate, or clobetasol propionate. Therapeutic effects can also be improved when the organic acid salts of suplatast are used in combination with antiphlogistic enzymes. Examples of antiphlogistic enzymes include serrapeptase, lysozyme chloride, semialkaline proteinase, proctase, and pancreatine, with serrapeptase being preferred.

When interstitial cystitis is treated by use of any one of the therapeutic drugs of the present invention, hydrodistention therapy may also be used in combination from the viewpoints of improved diagnosis and therapy.

The therapeutic drugs of the present invention may take a variety of administration forms including, for example, peroral agents, injections, suppositories per rectum, and external agents (ointments, patches, etc.). Products of these dosage forms may be prepared by customary methods per se known by persons skilled in the art. When peroral solid preparations are manufactured, one or more of the active ingredients are mixed with a vehicle, and optionally, a binder, a disintegrant, a lubricant, a colorant, a sweetener, a flavoring agent, or similar agents, and the resultant mixture is processed into tablets, coated tablets, granules, powders, capsules, etc. by customary methods. When peroral liquid preparations are manufactured, one or more of the active ingredients are mixed with a sweetener, a buffer, a stabilizer, a flavoring agent, or similar agents, and the resultant mixture is processed into, by customary methods, liquid medicine, syrup, etc. When injections are manufactured, one or more of the active ingredients are mixed with a pH regulator, a buffer, a stabilizer, an isotonic agent, a local anesthetic drug, or similar agents, and the resultant mixture is processed into injection products for subcutaneous injection, intramuscular injection, or intravenous injection. Suppositories per rectum are prepared by mixing one or more of the active ingredients along with an excipient, optionally with a surfactant, etc., followed by a routine process for manufacturing suppositories. When ointments, such as in the form of paste, cream, or gel, are prepared, a base, a stabilizer, a humectant, a preservative, etc., which are generally employed in the manufacture of ointments are added to one or more of the active ingredients of the present invention, followed by mixing and processing into ointment products by customary methods. Examples of bases include white Vaseline, paraffin, glycerin, cellulose derivatives, polyethylene glycol, silicone, and bentonite. Examples of preservatives include methyl paraoxybenzoate, ethyl paraoxybenzoate, and propyl paraoxybenzoate. When patches are produced, the above-mentioned ointment, cream, gel, paste, etc. are applied onto a customary support by a known method. Supports are preferably woven or nonwoven fabrics made of cotton, staple fiber, or chemically synthetic fiber, and films and foamed sheets prepared from soft vinyl chloride, polyethylene, or polyurethane.

When an organic acid salt of spulatast, and a steroid and/or an antiphlogistic enzyme both serve as active ingredients, the drug of the present invention may take a single dosage form containing both. Alternatively, the drug may be prepared into two separate forms taken via the same administration route, individually containing the above ingredients (for example, both being peroral agents). It is also possible for one to be formulated as a peroral agent, and the other to be prepared as an injection.

The amount of the organic acid salt of spulatast to be incorporated into the above-mentioned unit dosage form varies with the patient's symptoms, the dosage forms, etc. It is generally preferred that the salt be incorporated into a unit dosage in an amount of about 5–1,000 mg for peroral agents, about 0.1–500 mg for injections, and about 5–1,000 mg for suppositories and external agents. Also, the daily dose of the organic acid salt of spulatast prepared into any one of the above dosage forms is not unequivocally determined, as it may differ depending on the symptoms, etc. In general, preferable daily doses fall within the range of about 0.1–5,000 mg. The dose of a steroid is appropriately determined according to the steroid species. Typically, preferable daily doses of a steroid fall within the range of about 0.1–300 mg, which may be reduced gradually. The dose of an antiphlogistic enzyme is appropriately determined according to the enzyme species. Typically, preferable daily doses of an antiphlogistic enzyme fall within the range of about 0.1–100 mg, which may be reduced gradually.

EXAMPLES

The present invention will next be described by way of examples, which should not be construed as limiting the invention thereto.

Preparation Example 1 Tablet

| | |
|---|---|
| spulatast tosylate | 50 mg |
| cornstarch | 50 mg |
| microcrystalline cellulose | 50 mg |
| hydroxypropyl cellulose | 15 mg |
| lactose | 47 mg |
| talc | 2 mg |
| magnesium stearate | 2 mg |
| ethyl cellulose | 30 mg |
| unsaturated glyceride | 2 mg |
| titanium dioxide | 2 mg |

Tablets (250 mg/tablet) of the above-described composition were prepared by employing a conventional method.

Preparation Example 2 Granule

| | |
|---|---|
| spulatast metanesulfonate | 300 mg |
| lactose | 540 mg |
| cornstarch | 100 mg |
| hydroxypropyl cellulose | 50 mg |
| talc | 10 mg |

Granules (1,000 mg/package) of the above-described composition were prepared by employing a conventional method.

Preparation Example 3 Capsule

| | |
|---|---|
| spulatast tosylate | 100 mg |
| lactose | 30 mg |
| cornstarch | 50 mg |
| microcrystalline cellulose | 10 mg |
| magnesium stearate | 3 mg |

Capsules (193 mg/capsule) of the above-described composition were prepared by employing a conventional method.

Preparation Example 4 Injection

| | |
|---|---|
| spulatast camphor sulfonate | 100 mg |
| sodium chloride | 3.5 mg |
| distilled water | suitable amount |

Injections (2 ml/ampule) of the above-described composition were prepared by employing a conventional method.

Preparation Example 5 Syrup

| spulatast maleate | 200 mg |
|---|---|
| purified sucrose | 60 g |
| ethyl para-hydroxybenzoate | 5 mg |
| butyl para-hydroxybenzoate | 5 mg |
| fragrance | suitable amount |
| colorant | suitable amount |
| purified water | suitable amount |

A syrup of the above-described composition was prepared by employing a conventional method.

Preparation Example 6 Suppository

| spulatast tosylate | 300 mg |
|---|---|
| Witepsol W-35 | 1400 mgg |

(Witepsol: registered trademark, product of Dynamite Nobel AG: a mixture of mono-, di-, and tri-glycerides of saturated fatty acids which encompass those acids from lauric acid to stearic acid)

Suppositories of the above-described composition were prepared by employing a conventional method.

Example 1

An Interstitial Cystitis Model Induced by Injecting Hydrochloric Acid into the Bladder Experimental Method:

Three groups of rats were established according to body weight. Under anesthesia with pentobarbital (50 mg/kg i.p.), each rat in the control group and the spulatast tosylate administration group had 0.4N HCl injected into the bladder, and each rat in the untreated group received an injection of saline (0.2 ml) also into the bladder. From the day following the injection, administration of the drug was started. To each rat in the spulatast tosylate administration group, spulatast tosylate (100 mg/kg) was administered, and to each of the other groups, distilled water (5 ml/kg) was administered, in both cases orally, for seven days. On the eighth day after injection into the bladder, the function of the bladder was checked under urethane anesthesia (1.0 g/kg i.p.). The lower abdomen of each rat was shaved with a razor and the body was fixed in the dorsal position. Subsequently, the middle of the abdomen was incised for about four centimeters, thereby exposing the bladder. Thereafter, a small incision was made at a selected site on the top of the bladder where a relatively thin network of blood vessels and nerves was present. A polyethylene catheter (PE-50: product of NIHON BECTON DICKINSON) was inserted about 10 mm into the bladder, and the opening was closed with a suture. At the other end of the catheter which had been inserted into the bladder and fixed, pressure was measured by means of a pressure amplifier (Model 2238; product of NIHON DENKI SAN'EI) through a pressure transducer (disposable blood pressure monitoring life kit DX-360; product of NIHON KODEN). The end was also connected to a continuous injector (TERUFUSION syringe pump STC-521; product of Terumo Corp.) equipped with a dedicated syringe through a thermostatic apparatus for maintaining the temperature of the saline (BLOODWARMER TM-90, product of TORAY Industries, Inc.) via a three-way stopcock. Saline was injected at a rate of 3.0 ml/hr into the bladder, and the internal pressure of the bladder was recorded through a Mac Lab system (data recording and analysis software, chart program V 3.3 (AD Instruments Pty Ltd.)). Simultaneously, each rat was fixed in a dorsal position on a BALLMAN CAGE (custom-made acrylic product; YAMASHITA GIKEN), and urine quantity was measured by means of a scale (HF-200; product of A&D Ltd.) and recorded. From a cystometrogram and a curve showing the scaled weight of urine during the 20 minutes after commencement of injection into the bladder, the following parameters, which represent bladder function, were read: basal pressure of the bladder, micturition threshold pressure, maximum micturition pressure of the bladder, urinary frequency, micturition interval, micturition volume per micturition, and bladder capacity. Bladder compliance (bladder capacity/micturition threshold pressure) was also calculated for evaluation. The results are all represented by mean value±standard error (mean±S.E.). A significant difference when compared to the control group was obtained by means of a Student's t-test, where instances in which $p<0.05$ were considered to be significantly different (*: $p<0.05$, **: $p<0.01$).

As is apparent from Table 1, administration of spulatast tosylate significantly improves various symptoms accompanying interstitial cystitis, i.e., urinary frequency, micturition volume, bladder capacity, etc.

TABLE 1

| | Test results: | | | |
|---|---|---|---|---|
| | Basal pressure bladder (mmHg) | Micturition threshold pressure (mmHg) | Max. micturiction the bladder (mmHg) | Urinary frequency (times/20 min) |
| Untreated group (n = 7) | 6.6 ± 0.9* | 10.1 ± 0.9 | 26.2 ± 1.9 | 4.0 ± 0.8** |
| Control group (n = 7) | 12.9 ± 2.3 | 14.8 ± 2.4 | 30.4 ± 2.2 | 12.6 ± 4.6 |
| Suplatast tosylate administration group (100 mg/kg) (n = 8) | 8.6 ± 1.6 | 11.0 ± 1.1 | 25.1 ± 2.8 | 4.6 ± 1.9** |

TABLE 1-continued

|  | Micturition interval (min) | Test results: Micturition Volume (mg) | Bladder capacity (ml) | Bladder compliance (ml/mmHg) |
|---|---|---|---|---|
| Untreated group (n = 7) | 6.3 ± 1.9 | 0.29 ± 0.09* | 0.31 ± 0.09 | 0.0246 ± 0.0067* |
| Control group (n = 7) | 2.4 ± 0.4 | 0.08 ± 0.02 | 0.12 ± 0.02 | 0.0070 ± 00022 |
| Suplatast tosylate administration group (100 mg/kg) (n = 8) | 5.3 ± 1.0* | 0.22 ± 0.04** | 0.27 ± 0.05* | 0.0216 ± 0.0048* |

Example 2

A Hemorrhagic Cystitis Model Induced by Cyclophosphamide

Experimental Method:

Three groups of rats were established according to body weight. Each rat in the control group and the suplatast tosylate administration group was peritoneally administered with 150 mg/kg cyclophosphamide, and each rat in the untreated group was intraperitoneally administered with saline (5 ml/kg). Each rat in the suplatast tosylate administratiLon-group was orally given 100 mg/kg suplatast tosylate, and distilled water (5 ml/kg) was given to each rat in the other groups, in both cases orally for four days. On the fifth day following the administration of cyclophosphamide, the function of the bladder was checked. The bladder function test was performed in a manner similar to that described for the cystitis model created by use of HCl.

As shown in Table 2, it was revealed that administration of suplatast tosylate significantly improves various conditions accompanying hemorrhagic cystitis, including basal pressure of the bladder, micturition threshold pressure, and maximum micturition pressure of the bladder.

TABLE 2

|  | Test results: | | | |
|---|---|---|---|---|
|  | Basal pressure of the bladder (mmHg) | Micturition threshold pressure (mmHg) | Max. micturition pressure of the bladder (mmHg) | Urinary frequency (times/20 min) |
| Untreated group (n = 5) | 4.9 ± 0.2** | 9.4 ± 0.7* | 24.1 ± 2.6** | 2.2 ± 0.4* |
| Control group (n = 5) | 24.6 ± 4.4 | 24.5 ± 5.1 | 40.7 ± 2.6 | 8.0 ± 2.1 |
| Suplatast tosylate administration group (100 mg/kg) (n = 5) | 9.4 ± 2.0* | 11.6 ± 1.1* | 27.5 ± 1.8* | 3.8 ± 1.9 |

|  | Micturition interval (min) | Micturition Volume (mg) | Bladder capacity (ml) | Bladder compliance (ml/mmHg) |
|---|---|---|---|---|
| Untreated group (n = 5) | 9.01 ± 1.03** | 0.46 ± 0.06* | 0.45 ± 0.05* | 0.0469 ± 0.0066** |
| Control group (n = 5) | 3.56 ± 1.03 | 0.21 ± 0.05 | 0.18 ± 0.05 | 0.0089 ± 00041 |
| Suplatast tosylate administration group (100 mg/kg) (n = 5) | 11.25 ± 4.43 | 0.62 ± 0.19 | 0.56 ± 0.22 | 0.0461 ± 0.0176 |

Example 3

Histopathological Evaluation in an Interstitial Cystitis Model

Experimental Method:

Three groups of rats were established according to body weight. Under anesthesia with pentobarbital (50 mg/kg i.p.), each rat in the control group and the suplatast tosylate administration group was injected with 0.4N HCl into the bladder, and each rat in the untreated group was injected with saline (0.2 ml) into the bladder. From the day following injection into the bladder, administration of the drug was started. To each rat in the suplatast tosylate administration group, suplatast tosylate (100 mg/kg) was administered, and to each of the other groups, distilled water (5 ml/kg) was administered, in both cases orally for seven days. On the eighth day after injection into the bladder, the bladders were removed, and tissue samples thereof were fixed with 10% formalin. The fixed tissue samples were first cut and then embedded in paraffin for slicing. The slices were stained with eosin, and observed under an optical microscope.

As is apparent from Table 3, suplatast tosylate was found to be histopathologically effective in the treatment of interstitial cystitis.

TABLE 3

| Site/findings | Group Degree of change | Untreated group n = 4 | | | | Control group n = 5 | | | | Suplatast tosylate administration group n = 4 | | | |
|---|---|---|---|---|---|---|---|---|---|---|---|---|---|
| | | − | + | ++ | +++ | − | + | ++ | +++ | − | + | ++ | +++ |
| <Transitional epithelium> | | | | | | | | | | | | | |
| Thickening Inflammatory cells Infiltration | | 4 | 0 | 0 | 0 | 1 | 1 | 3 | 0 | 3 | 1 | 0 | 0 |
| <Lamina propria> | | | | | | | | | | | | | |
| Proliferation of spindle shaped cells | | 4 | 0 | 0 | 0 | 4 | 1 | 0 | 0 | 4 | 0 | 0 | 0 |
| Edema | | 4 | 0 | 0 | 0 | 1 | 1 | 3 | 0 | 4 | 0 | 0 | 0 |
| Inflammatory cells Infiltration | | 4 | 0 | 0 | 0 | 1 | 3 | 1 | 0 | 4 | 0 | 0 | 0 |
| <Muscle layers> | | | | | | | | | | | | | |
| Interstitial edema | | 4 | 0 | 0 | 0 | 1 | 4 | 0 | 0 | 4 | 0 | 0 | 0 |
| Inflammatory cells Infiltration | | 4 | 0 | 0 | 0 | 1 | 3 | 1 | 0 | 4 | 0 | 0 | 0 |
| | | 4 | 0 | 0 | 0 | 1 | 3 | 1 | 0 | 4 | 0 | 0 | 0 |

Degree of change: −; no change, +; slight change, ++; moderate change, +++; great change

Example 4

A 45-year old woman visited the clinic with complaints of urinary urgency, urinary frequency, and abdominal pain. From the results of urologic laboratory examination and biopsy of the bladder membrane, she was diagnosed as suffering from interstitial cystitis.

TABLE 4

| Biopsy of bladder membrane | T cell (+) upper layer, B cell (+) lower layer |
|---|---|
| Bladder capacity | 50–60 ml |
| Hydrodistention therapy | employed in combination |

The regimen during hospitalization was oral administration of suplatast tosylate (100 mg capsules, trade name: IPD capsule 100, product of Taiho Pharmaceutical Co., Ltd.) thrice daily in combination with, but only for the initial one month, oral administration of a steroid (Prednine (active ingredient: prednisolone; Shionogi & Co., Ltd.); gradually decreasing from the initial dose of 60 mg/day to 15 mg/day at the end of that month).

Findings after 7 months are summarized below. The patient was discharged. Subsequently, she was on a regimen of peroal administration of suplatast tosylate alone with no recurrence.

TABLE 5

| Volume of urine per micturition | 150 ml |
|---|---|
| Elimination of pollakiuria and miction pain | |

Example 5

A 23-year-old woman visited the clinic complaining of urinary frequency of 60 times or more a day. From the results of urologic laboratory examination and biopsy of the bladder membrane, she was diagnosed as suffering from interstitial cystitis.

TABLE 6

| Biopsy of bladder membrane | T cell (+) upper layer, B cell (+) lower layer antinuclear antibody (+) |
|---|---|
| Volume of the bladder | 50–60 ml |
| Hydrodistention therapy | employed in combination |

The regimen during hospitalization was oral administration of suplatast tosylate (100 mg capsules, trade name: IPD capsule 100, product of Taiho Pharmaceutical Co., Ltd.) thrice daily in combination with, but only for the initial one month, oral administration of a steroid (Prednine (active ingredient: prednisolone; Shionogi & Co., Ltd.); gradually decreasing from the initial dose of 60 mg/day to 15 mg/day at the end of that month).

Two months later, the bladder capacity was 300 ml, thus showing a remarkable improvement.

Example 6

A 23-year-old woman visited the clinic with complaints of pain in the lower abdomen and urinary frequency. The bladder capacity was 50–60 ml, and from the results of urologic laboratory examination and biopsy of the bladder membrane, she was diagnosed as suffering from interstitial cystitis. After suplatast tosylate (100 mg capsules, trade name: IPD capsule 100, product of Taiho Pharmaceutical Co., Ltd.) was orally administered to her thrice daily for one month, the volume of urine per voiding increased. The pain in the lower abdomen and urinary frequency were also ameliorated.

Example 7

A 51-year-old woman visited the clinic with complaints of bladder pain and urinary frequency (50 ml urine per voiding). From the results of urologic laboratory examination and biopsy of the bladder membrane, she was diagnosed as suffering from interstitial cystitis. She was treated by oral administration of suplatast tosylate (100 mg capsules, trade name: IPD capsule 100, product of Taiho Pharmaceutical Co., Ltd.) thrice daily for three months, in combination with, but only for the initial one month, oral administration of a steroid (Prednine (active ingredient: prednisolone; Shionogi & Co., Ltd.); gradually decreasing from the initial dose of 60 mg/day to 15 mg/day at the end of that month). Eighty days later, the volume of urine per voiding was 200 ml, and urinary frequency and miction pain disappeared.

Example 8

A 23-year-old woman had been suffering pollakiuria and miction pain for three months. She visited a neighborhood clinic, and was not diagnosed as having cystitis but as suffering from mentally-evoked symptoms, and was prescribed a crude drug (Selshin-renji-in). The symptoms were not alleviated, and she was listed as an employee to be involved in her company's restructuring program, due to inability to adapt to work.

The micturition frequency was 1–2 times per 30 minutes, night and day, which prevented sound sleeping. From biochemical examinations of blood and urine, and also from cystoscopy, the following regimen was applied: peroral administration of suplatast tosylate (100 mg capsules, trade name: IPD capsule 100, product of Taiho Pharmaceutical Co., Ltd.) thrice daily, in combination with, but for 2 weeks only, oral administration of an antiphlogistic enzyme agent (Dazen (active ingredient: serrapeptase, product of Takeda Chemical Industries, Ltd.) at a daily dose of 3 tablets (effective dose: 15 mg serrapeptase equivalent)). One month later, miction pain disappeared, and urinary frequency was alleviated to voiding around 15 times a day.

Example 9

A 33-year-old woman visited the clinic with complaints of urinary frequency every 30 minutes and bladder pain. From clinical examinations such as biochemical examinations of blood and urine, she was diagnosed as suffering from intractable pollakiuria associated with cystitis.

She was treated by oral administration of suplatast tosylate (100 mg capsules, trade name: IPD capsule 100, product of Taiho Pharmaceutical Co., Ltd.) thrice daily. Eight months later, her urine data became normal, and urinary frequency was ameliorated.

Example 10

A 62-year-old woman visited the clinic complaining of urinary frequency. From biochemical examinations of blood and urine, and also from cystoscopy, she was diagnosed as suffering from intractable pollakiuria associated with chronic cystitis. She was treated by oral administration of suplatast tosylate (100 mg capsules, trade name: IPD capsule 100, product of Taiho Pharmaceutical Co., Ltd.) thrice daily. Two weeks later, the symptoms of pollakiuria were ameliorated.

Example 11

A 54-year-old man visited the clinic with complaints of miction pain and urinary frequency. From clinical examinations such as biochemical examinations of blood and urine, he was diagnosed as suffering from prostatitis. He was treated by oral administration of suplatast tosylate (100 mg capsules, trade name: IPD capsule 100, product of Taiho Pharmaceutical Co., Ltd.) thrice daily. One month later, he had a significantly lowered IgE value, with symptoms of pollakiuria and miction pain having disappeared.

Example 12

A 47-year-old man visited the clinic with complaints of a sense of residual urine, urinary frequency at night, morning post-micturition pain, and discomfort and pain in the lower abdomen. He had prostatic hypertrophy, but administration of ordinary therapeutic drugs for the treatment of prostatic hypertrophy had no effect at all. He was later diagnosed as suffering from chronic prostatitis. He was treated by oral administration of suplatast tosylate (100 mg capsules, trade name: IPD capsule 100, product of Taiho Pharmaceutical Co., Ltd.) thrice daily. Two weeks later, the symptoms of pollakiuria, post-micturition pain, etc. were alleviated by about half.

Example 13

A 78-year-old man had a bladder cancer (transitional cell carcinoma pT1b, grade 3) associated with pollakiuria and bladder pain. After he underwent transurethral resection of the bladder tumor (TUR-Bt), he experienced continued pollakiuria and bladder pain. He was treated by oral administration of suplatast tosylate (100 mg capsules, trade name: IPD capsule 100, product of Taiho Pharmaceutical Co., Ltd.) thrice daily. After four months, the symptoms of pollakiuria and bladder pain had disappeared (since then one year has elapsed with no further symptoms).

Example 14

An 82-year-old man had a bladder cancer (transitional cell carcinoma, carcinoma in situ (CIS)) associated with pollakiuria and bladder pain. He was treated by oral administration of suplatast tosylate (100 mg capsules, trade name: IPD capsule 100, product of Taiho Pharmaceutical Co., Ltd.) thrice daily. After six months, symptoms of pollakiuria and bladder pain had disappeared.

Example 15

A 60-year-old woman underwent a surgical operation for uterine carcinoma twenty years previously, followed by postoperative radiotherapy. She visited the clinic with complaints of hematuria, pollakiuria, and urinary incontinence. Petechial hemorrages as observed in interstitial cystitis was confirmed by cystoscopy. She was diagnosed as suffering from radiation cystitis with low compliance of the urinary bladder, and treated by oral administration of suplatast tosylate (100 mg capsules, trade name: IPD capsule 100, product of Taiho Pharmaceutical Co., Ltd.) thrice daily. Six months later, the symptoms had disappeared.

Example 16

A 53-year-old man had an contracted bladder (20 ml) caused by bladder tuberculosis, and suffered from bladder pain. He was treated by oral administration of suplatast tosylate (100 mg capsules, trade name: IPD capsule 100, product of Taiho Pharmaceutical Co., Ltd.) thrice daily. After six months, the bladder capacity had increased to 150 ml with alleviated bladder pain.

Example 17

To a patient who had undergone 8 courses of treatment for transitional cell carcinoma (BCG Immunoplader 40 mg/saline 40 ml) and later had complaints of pollakiuria and bladder pain, suplatast tosylate (100 mg capsules, trade name: IPD capsule 100, product of Taiho Pharmaceutical Co., Ltd.) was administered thrice daily. After three months, the symptoms had disappeared.

Industrial Applicability

The present invention has enabled treatment of various diseases of the lower urinary tract system causing micturition disorders, such as interstitial cystitis and prostatitis, which arise from unelucidated causes and are thus regarded as intractable diseases.

What is claimed is:

1. A therapeutic drug composition for a disease of the lower urinary tract system which causes a micturition disorder, comprising as an active ingredient, a therapeutically effective amount of an organic acid salt of [2-[4-(3-ethoxy-2-hydroxypropoxy)phenylcarbamoyl]ethyl]-dimethylsulfonium.

2. A therapeutic drug composition according to claim 1, wherein the disease of the lower urinary tract system is a disease which induces edemas, infiltration of inflammatory cells, or proliferation of spindle cells in the lower urinary tract.

3. A therapeutic drug composition according to claim 1, wherein the disease of the lower urinary tract system is a disease which induces edemas, infiltration of inflammatory cells, or proliferation of spindle cells in the bladder or prostate.

4. A therapeutic drug composition according to claim 1, wherein the disease of the lower urinary tract system is cystitis, prostatitis, or prostatic hypertrophy.

5. A therapeutic drug composition according to claim 1, wherein the disease of the lower urinary tract system is selected from the group consisting of acute or chronic cystitis, interstitial cystitis, hemorrhagic cystitis, radiation cystitis, bladder tuberculosis, and acute or chronic prostatitis.

6. A therapeutic drug composition according to any one of claims 1 to 5, wherein the active ingredient is [2-[4-(3-ethoxy-2-hydroxypropoxy)phenylcarbamoyl]ethyl] dimethylsulfonium p-toluenesulfonate.

7. A therapeutic drug composition according to any one claims 1 to 5, which further contains, as active ingredients, a steroid and/or an antiphlogistic agent.

8. A therapeutic drug composition for a micturition disorder containing, as an active ingredient, a therapeutically effective amount of an organic acid salt of [2-[4-(3-ethoxy-2-hydroxypropoxy)phenylcarbamoyl]ethyl]-dimethylsulfonium.

9. A therapeutic drug composition according to claim 8, wherein the active ingredient is [2-[4-(3-ethoxy-2-hydroxypropoxy)phenylcarbamoyl]ethyl] dimethylsulfonium p-toluenesulfonate.

10. A therapeutic drug composition according to any one of claims 8 or 9, which further contains, as active ingredients, a steroid and/or an antiphlogistic agent.

11. A therapeutic drug composition according to any one of claims 8 or 9, which is used for the treatment of a micturition disorder caused by lesions in the blader wall or urethral obstructive lesions.

12. A therapeutic drug composition according to any one of claims 8 or 9, which is used for the treatment of a micturition disorder caused by a disease selected from the group consisting of acute or chronic cystitis, interstitial cystitis, hemorrhagic cystitis, radiation cystitis, bladder tuberculosis, bladder cancer, and acute or chronic prostatitis.

13. A therapeutic drug composition according to any one of claims 8 or 9, wherein, the micturition disorder is pollakiuria, miction pain, or bladder pain.

14. A method for treatment of a disease of the lower urinary tract system which causes a micturition disorder, characterized by administering a therapeutically effective amount of an organic acid salt of [2-[4-(3-ethoxy-2-hydroxypropoxy)phenylcarbamoyl]ethyl]-dimethylsulfonium.

15. A method according to claim 14, wherein the disease of the lower urinary tract system is a disease which induces edemas, infiltration of inflammatory cells, or proliferation of spindle cells in the lower urinary tract.

16. A method according to claim 14, wherein the disease of the lower urinary tract system is a disease which induces edemas, infiltration of inflammatory cells, or proliferation of spindle cells in the bladder or prostate.

17. A method according to claim 14, wherein the disease of the lower urinary tract system is cystitis, prostatitis, or prostatic hypertrophy.

18. A method according to claim 14, wherein the disease of the lower urinary tract system is selected from the group consisting of acute or chronic cystitis, interstitial cystitis, hemorrhagic cystitis, radiation cystitis, bladder tuberculosis, and acute or chronic prostatitis.

19. A method according to any one of claims 14 to 18, wherein the organic acid salt of [2-[4-(3-ethoxy-2-hydroxypropoxy)phenylcarbamoyl]ethyl]dimethysulfonium is [2-[4-(3-ethoxy-2-hydroxypropoxy)phenylcarbamoyl] ethyl]-dimethylsulfonium p-toluenesulfonate.

20. A method according to any one of claims 14 to 18, which further comprises administration of a steroid and/or an antiphlogistic agent.

21. A method for treatment of a micturition disorder, characterized by administering a therapeutically effective amount of an organic acid salt of [2-[4-(3-ethoxy-2-hydroxypropoxy)phenylcarbamoyl]ethyl]-dimethylsulfonium.

22. A method according to claim 21, wherein the organic acid salt of [2-[4-(3-ethoxy-2-hydroxypropoxy)-phenylcarbamoyl]ethyl]dimethylsulfonium is [2-[4-(3-ethoxy-2-hydroxypropoxy)phenylcarbamoyl]ethyl] dimethylsulfonium p-toluenesulfonate.

23. A method according to claim 21 or 22, which further comprises administering a steroid and/or an antiphlogistic agent.

24. A method according to any one of claims 21 or 22, wherein the micturition disorder is a disorder caused by lesions in the bladder wall or urethral obstructive lesions.

25. A method according to any one of claims 21 or 22, wherein the micturition disorder is caused by a disease selected from the group consisting of acute or chronic cystitis, interstitial cystitis, hemorrhagic cystitis, radiation cystitis, bladder tuberculosis, bladder cancer, and acute or chronic prostatitis.

26. A method according to any one of claims 21 or 22, wherein the micturition disorder is pollakiuria, miction pain, or bladder pain.

27. A therapeutic drug composition according to any one of claims 1 to 5, effective in an animal.

28. A therapeutic drug composition according to claim 27, wherein said animal is a human.

29. A therapeutic drug composition according to any one of claims 8 or 9, effective in a mammal.

30. A therapeutic drug composition according to claim 29, wherein said mammal is a human.

31. A method according to any one of claims 14 to 18, which comprises administering a therapeutically effective amount of the organic acid salt of [2-[4-(3-ethoxy-2-hydroxypropoxy)phenylcarbamoyl]ethy]dimethylsulfonium to a mammal.

32. A method according to any one of claims 14 to 18, which comprises administering a therapeutically effective amount of the organic acid salt of [2-[4-(3-ethoxy-2-hydroxypropoxy)phenylcarbamoyl]ethyl]dimethylsulfonium to a mammal.

33. A method according to any one of claims 21 or 22, which comprises administering a therapeutically effective amount of the organic acid salt of [2-[4-(3-ethoxy-2-hydroxypropoxy)phenylcarbamoyl]ethyl]dimethylsulfonium to a mammal.

34. A method according to claim 33 wherein said mammal is a human.

* * * * *